(12) United States Patent
Brown

(10) Patent No.: US 9,072,753 B1
(45) Date of Patent: Jul. 7, 2015

(54) GARGLE METHOD TO REDUCE THE DURATION OF COMMON COLD SYMPTOMS

(76) Inventor: Amy C. Brown, Honolulu, HI (US)

(*) Notice: Subject to any disclaimer, the term of this patent is extended or adjusted under 35 U.S.C. 154(b) by 437 days.

(21) Appl. No.: 12/930,155

(22) Filed: Dec. 29, 2010

Related U.S. Application Data

(63) Continuation of application No. 11/894,350, filed on Aug. 21, 2007, now abandoned, which is a continuation of application No. 10/935,538, filed on Sep. 7, 2004, now abandoned, which is a continuation-in-part of application No. 10/665,345, filed on Sep. 20, 2003, now abandoned, which is a continuation-in-part of application No. 09/821,653, filed on Mar. 28, 2001, now Pat. No. 6,641,801.

(51) Int. Cl.
*A61K 36/63* (2006.01)

(52) U.S. Cl.
CPC ........................................ *A61K 36/63* (2013.01)

(58) Field of Classification Search
USPC ..................................................... 424/58, 769
IPC ....................................................... A61K 36/63
See application file for complete search history.

(56) References Cited

U.S. PATENT DOCUMENTS

| | | | | |
|---|---|---|---|---|
| 5,503,825 A * | 4/1996 | Lane | ................ | 424/64 |
| 5,622,724 A * | 4/1997 | Bryce-Smith | ................. | 424/641 |
| 5,714,150 A * | 2/1998 | Nachman | ...................... | 424/769 |
| 6,117,844 A * | 9/2000 | Fredrickson | .................... | 514/27 |
| 6,165,475 A * | 12/2000 | Crea et al. | ...................... | 424/769 |
| 6,165,494 A * | 12/2000 | Picciano | ........................ | 424/434 |
| 6,455,070 B1 * | 9/2002 | Voorhees et al. | ............. | 424/465 |
| 6,455,580 B1 * | 9/2002 | Fredrickson | .................. | 514/460 |
| 6,676,980 B2 * | 1/2004 | Quintanilla Almagro et al. | ............................. | 424/769 |
| 2001/0018077 A1 * | 8/2001 | Shaner | ......................... | 424/726 |
| 2002/0064542 A1 * | 5/2002 | Deckner et al. | ................ | 424/404 |
| 2003/0108651 A1 * | 6/2003 | Crea | ............................. | 426/615 |

FOREIGN PATENT DOCUMENTS

GB      1256092     * 12/1971

OTHER PUBLICATIONS

Privitera, Olive Leaf Extract—A New?Old Healing Bonanza for Mankind, curezone.com/foods/oliveleaf webstite, 1996, 20 pages.*
Barrett, Homeophaty: The Ultimate Facke, quackwatch.com webstite, 1999, 6 pages.*

* cited by examiner

*Primary Examiner* — Chris R Tate
(74) *Attorney, Agent, or Firm* — Barbara E. Johnson, Esq.

(57) ABSTRACT

A method of reducing the presence, duration, severity, or symptoms of the common cold entails the administration of a nonalcoholic antiviral remedy to a subject in need of such treatment, preferably in the form of a gargle.

6 Claims, No Drawings

GARGLE METHOD TO REDUCE THE DURATION OF COMMON COLD SYMPTOMS

CROSS REFERENCE TO RELATED APPLICATIONS

This application is a continuation of U.S. patent application Ser. No. 11/894,350 filed Aug. 21, 2007 now abandoned, which is a continuation of U.S. patent application Ser. No. 10/935,538, filed Sep. 7, 2004 now abandoned, which is a continuation-in-part of U.S. patent application Ser. No. 10/665,345 filed Sep. 20, 2003 now abandoned, which is a continuation-in-part of U.S. patent application Ser. No. 09/821,653 filed Mar. 28, 2001, now U.S. Pat. No. 6,641,801, which are incorporated herein by reference in their entirety.

BACKGROUND OF THE INVENTION

1. Field of the Invention

This invention relates to methods and preparations for reducing the duration of common colds and reducing the severity of common cold symptoms. More particularly, this invention relates to the remedies comprising medicaments which shorten the duration of common colds, reduce the severity of symptoms, and/or otherwise beneficially treat common colds. These ingredients are believed to be antiviral agents. Such ingredients are combined with a pharmaceutically acceptable carrier suitable for the chosen method and form of administration. The most preferred method of administration is exposure of the oral and oral pharyngeal tissues to the agents for a period of time sufficient for the remedy to be exposed to the oral and oral pharyngeal mucous membranes, such as by gargling. The preferred forms of the remedy for administration therefore include mouthwashes and lozenges. In these embodiments, the preparation preferably includes a suitable carrier, and other ingredients such as flavors, stabilizers, lubricants and additional natural or artificial sweeteners.

2. General Background

The "common cold" and, simply, "cold" are time-honored phrases used by both physicians and lay persons alike for the identification of upper respiratory illness caused by viral infection. Colds are most often acute, minor illnesses which eventually subside without treatment for the infection itself. However, common colds are still a major public health problem.

Colds are the most common acute illness in the United States of America and generally account for about one-half of all absences from school and work. Many if not all of the viruses that cause the common cold are easily transmitted from host to host. For example, such viruses may be spread in aerosols, so they may be spread through the air by, e.g., sneezing. Additionally, a number of viruses can survive out of a host's body for extended periods of time, and so can be transmitted by hands and objects. Further, a virus that causes only a minor cold in one host may threaten the life of another host by causing influenza, a much more serious upper respiratory infection that may be fatal. P. R. Murray et al., Medical Microbiology, 2.sup.nd ed., Mosby-Year Book, Inc., p. 723, 616-7 (1994).

Since the discovery of rhinovirus in 1956, a considerable body of knowledge has been acquired on the etiology and epidemiology of common colds and influenzas. It is known that the common cold is not a single entity, but rather is a group of diseases caused by members of several families of viruses including adenoviruses, influenza viruses, parainfluenza viruses, rhinoviruses, respiratory syncytial viruses, enteroviruses, echoviruses, coxsackieviruses, and coronaviruses. Much work has been performed in characterizing viruses which cause the common cold. For instance, the molecular biology of rhinoviruses, which causes at least 50% of all upper respiratory tract infections, is understood in great detail. Murray, pp. 723,616. For the purposes of this patent application only, "common cold" should be understood to embrace not only rhinoviral infection but influenza type conditions attributable to any of the above or similar viral etiologies.

In contrast, progress on the treatment of common colds has been slow despite these advances. Indeed, it has been believed that the only current cure for the common cold is the body's natural defenses and the passage of time.

Many over-the-counter remedies for the common cold only treat symptoms. There are over 200 different virus serotypes that can cause the common cold. For example, there are at least 100 serotypes of rhinoviruses alone. Murray p. 616, Rhinology 37(3):97-103, 1999. It is therefore not possible to build immunity to this many causes of the common cold. It is also difficult to develop remedies that are effective against such a large number of viruses. Therefore, symptomatic relief has been the traditional recourse.

These prescription or over-the-counter products which treat symptoms of the common cold usually contain one or more of the following drugs: antihistamines, decongestants, pain relievers (aspirin, acetaminophen, ibuprofen), cough suppressants, expectorants, and analgesics. These remedies do not reduce the duration of the common cold, are of limited effectiveness in relieving the symptoms of the cold, and are often accompanied by unwelcomed side effects.

The duration of the average cold varies greatly among individuals. Twenty-five percent of all colds last 14 days, but the average duration of a cold is 7 days, with or without treatment.

Treatment with interferon has been somewhat successful in limiting the progression of infection in common colds. However, interferon has many negative effects and cannot be administered for any length of time. Murray pp. 616-619.

Zinc ions have been reported to inhibit the replication of rhinoviruses. See, Korant B D et al., Nature 248:588-590 (1974). Recently, soluble and ionizable zinc compounds applied to the oral and oralpharyngeal mucosa have been used to treat common colds and have had some success in shortening the duration of the common cold. See, for example, U.S. Pat. Nos. 5,409,905; 5,286,748; 5,286,748; RE033465; and 4,956,385; to Eby III. See also U.S. Pat. No. 5,622,724 to Bryce-Smith and U.S. Pat. No. 4,684,528 to Godfrey. Eby claims that after seven days, 86% of 37 zinc-treated subjects were asymptomatic, compared with only 46% of 28 placebo-treated subjects. (Antimicrob. Agents Chemother. 25(1):20-4, 1984). Mossad's double-blind, placebo controlled study on zinc lozenges revealed that patients treated with zinc lozenges had colds averaging 4.4 days compared to 7.6 days for those on the placebo. (Ann Intern Med 125::81-88, 1996). However, treatment also causes side effects, such as nausea and bad-taste reactions. Mossad. The cold duration thus appears reduced by zinc treatment, but the reduction is not dramatic, especially given the average cold duration of 7 days.

Given the very limited success of current cold remedies, some people say that cold remedies today come no closer to curing the common cold than they did thousands of years ago. Thus there can be no question as to the need for an improved remedy that will shorten the duration of common colds.

Treatment

Common cold symptoms are largely the result of the inflammatory response to the viral infection, as described above, rather than the infection itself. Treatment of the common cold is primarily symptomatic. Common therapeutic agents include alpha-adrenergic agonist decongestants, antihistamines, analgesics, antipyrrhetics, and antitussives. There is also clinical experience and trials utilizing anticholinergic nasal sprays, mast cell stabilizers, and glucocorticoids (5,13). A variety of antiviral agents with in vitro activity have been ineffective (5). Trials using zinc lozenges show mixed results (14,15,16,17,18). Antibiotics are ineffective except for treating secondary or concurrent bacterial infections (19).

Botanical Remedies

There is growing interest in complementary medicine. *Echinacea* is a popular herbal remedy and is thought to reduce cold symptoms due to its ability to stimulate the immune system (20,21). Other herbs do have antiviral properties. In an ethnopharmacological screening of medicinal plants used in Yunnan province of China, 16 out of 31 plant extracts (52%) tested positive for antiviral activity (22). Few plant compounds have been formally tested for activity against rhinovirus. However there are reports of plan compounds having antiviral activity against other viruses; Gingyo-osan, Kampo (Japanese herbal), and *Tripterygium wilfordii* Hook, and elderberry are effective against influenza virus (23,24). Garlic has shown activity against herpes simplex, parainfluenza, vaccinia, vesicular stomatitis, and human rhinovirus type 2 (25). (+/−) Calanolide A, a coumarin derivative from the tropical rainforest tree *Calophyllum lanigerum*, is a novel non-nucleoside reverse transcriptase inhibitor for the Human Immunodeficiency Virus (26). Formulations of Calanolide A have been shown to be safe and well tolerated in healthy HIV-negative humans (27).

Mechanisms & Rationale

Evidence supporting anti-viral mechanisms for the above ingredients is based on the fact that certain compounds have antiviral action, many originating from botanical sources, and these have been utilized in the formulation of an antiviral gargle. Numerous plants have evidence of antiviral activity and a few of these are explained in detail below:

DESCRIPTION OF RELATED ART

Olive Whole Leaf (*Olea europaea*)

Fleming H P, Walter J R, Etchells J L. Antimicrobial properties of oleuropein and products of its hydrolysis from green olives. Applied Microbiology 26(5):777-782, 1973. "The presence of antimicrobial compounds in olives has been suspected for some time. DeCaro and Ligori found that the water solution remaining after oil was pressed from olives contained a substance which was inhibitory to several bacteria, most of which were gram positive. Recently, it was reported that salts of elenolic acid have antiviral properties. This acid is a hydrolysis product of oleuropein."

Renis H E. In vitro antiviral activity of calcium elenolate. Antimicrobial Agents and Chemotherapy 9:167-172, 1970. "Elenolic acid can be obtained . . . from the . . . extracts of various parts of the olive plant (*Olea europa*). We have found calcium elenolate to be virucidal for a broad spectrum of viruses in vitro . . . "

Soret M G. Antiviral activity of calcium elenolate on parainfluenza infection of hamsters. Antimicrobial Agents and Chemotherapy 9:160-166, 1970. "In the search for antiviral drugs, calcium elenolate was found to have in vitro activity against a variety of viruses."

Renis H E. Inactivation of myxoviruses by calcium elenolate. Antimicrobial Agents and Chemotherapy 8(2):194-199, 1975. "Calcium elenolate inactivates all myxoviruses so far tested."

Heinze J E, Hale A H, Carl P L. Specificity of the antiviral agent calcium elenolate. Antimicrobial Agents and Chemotherapy 8(4):421-425, 1975. "Calcium elenolate, a monoterpene which is isolated from aqueous extracts of the olive plant (*Olea europa*) . . . has been shown to be virucidal in vitro for a number of ribonucleic acid (RNA and deoxyribonucleic acid (DNA) viruses. Calcium elenolate inhibits the RNA-dependent DNA polymerases (reverse transcriptases) of both Moloney and Rauscher leukemia viruses . . . "

Hirschman S Z. Inactivation of DNA polymerases of murine leukaemia viruses of murine leukaemia viruses by calcium elenolate. Nature New Biology 238(87):277-279, 1972. "Calcium elenolate does have the advantage of being relatively nontoxic to cells in tissue culture at high concentrations and well tolerated in animals."

SUMMARY OF THE INVENTION

This invention provides methods and compounds for reducing the presence, duration, and severity of a common cold and of its symptoms by the administration of ethanol with or without homeopathic and/or herbal medicaments.

This invention also provides methods and compounds for reducing the presence, duration, and severity of a common cold and of its symptoms by the administration of nonalcoholic, antiviral remedy comprising of ingredients that are antiviral when applied topically—hydrogen peroxide, baking soda, vinegar, garlic, olive whole leaf, fennel, *eucalyptus*, zinc, ascorbic acid, food grade acids (citric, malic, oxalic, benoic, quinic, tannic, etc.) the unique combination of ingredients found in fresh ginger, citrus fruits (orange, mandarin, lemon, lime, etc.), cayenne pepper, and honey, or any combination thereof. The preferred route of administration of compositions identified in this paragraph is by gargling.

It is an object of this invention to provide effective treatments for the treatment of the common cold and its symptoms. Specifically, it is an object of this invention to provide remedies which reduce the duration of the cold, which reduce the severity or duration of one or more symptoms of the cold, and/or which prevent the common cold.

It is another object of this invention to overcome the problems and disadvantages associated with currently known approaches to treating the common cold and its symptoms.

Prior treatments for the cold have focused on alleviation of its symptoms. Very few remedies have had any success in reducing the duration of the cold. Further, prior treatments almost always contain drugs which cause side effects, which can be as debilitating as the cold itself. Unexpectedly, the present inventor has discovered that certain medicaments (ethanol with or without homeopathic and/or herb ingredients) can reduce the duration of the cold itself; as well as reducing the severity of the symptoms of the cold, and may also prevent infection by cold viruses. The remedy's active ingredient is ethanol with or without homeopathic and/or herb ingredients that are without known side effects and/or are given at homeopathic dosages, which appear to produce no side effects. The remedies of this invention therefore represent a novel treatment for the common cold, which treatment overcomes many of the disadvantages of the prior remedies.

In one embodiment, remedies according to the present invention include homeopathic concentrations of *Allium cepa* (red onion), *Salvia officinalis* (Sage), *Sambucus nigra* (elderberry), *Capsicum* (cayenne fruit), *Mentha piperta* (peppermint), and/or *Thymus serpyllum* (thyme); and also include perhaps one or a combination of the following ingredients: *Olea europaea* (olive whole leaf) *Lomatium dissectum* (lomatium root), *Rubis idaeus* (red raspberry leaf), and/or *Commiphora myrrha* (mrryh), *Trigonella foenum-graecum* (Fenugreek), *Pulmonaeia officinalis* (lungwort), *Althea officinalis* (marshmallow root tea), *Glycyrrhiza glabra* (licorice), *Ulmus rubra* (slippery elm bark), *Tabebuia avellanedae* (Pau d'arco), *Thymus vulgaeis* (thyme), *Melissa officinalis* (lemon oil), *Allium sativum* (garlic), and/or *capsicum annuum* (cayenne fruit).

In a preferred embodiment, remedies according to the present invention include homeopathic concentrations of *Allium cepa* (red onion), *Salvia officinalis* (Sage), *Sambucus nigra* (elderberry), *Capsicum* (cayenne fruit), *Mentha piperita* (peppermint), and/or *Thymus serpyllum* (thyme); and may also include one or a combination of *Olea europaea* (olive whole leaf), *Lomatium dissectum* (lomatium root), *Rubis idaeus* (red raspberry leaf), and/or *Commiphora myrrha* (mrryh).

In another preferred embodiment, the remedies comprise homeopathic concentrations singly and/or in combination of *Allium cepa* (red onion), *Salvia officinalis* (Sage), *Sambucus nigra* (elderberry), *Capsicum* (cayenne fruit), *Mentha piperita* (peppermint), *Thymus serpyllum* (thyme), and/or olive whole leaf (*Olea eruopaea*).

In yet another preferred embodiment, the remedies according to the present invention comprise one or a combination of *Olea europaea* (olive whole leaf), *Lomatium dissectum* (lomatium root), *Rubis idaeus* (red raspberry leaf), and/or *Commiphora myrrha* (myrrh).

In a particularly preferred embodiment, the remedies according to the present invention comprise homeopathic concentrations of at least one of *Allium cepa* (red onion), *Salvia officinalis* (Sage), *Sambucus nigra* (elderberry), *Capsicum* (cayenne fruit), *Mentha pipefita* (peppermint), and/or *Thymus serpyllum* (thyme) and also comprise at least one of *Olea europaea* (olive whole leaf), *Lomatium dissectum* (lomatium root), *Rubis idaeus* (red raspberry leaf), and/or *Commiphora myrrha* (myrrh).

In another particularly preferred embodiment, the remedies according to the present invention comprise homeopathic concentrations of *Allium cepa* (red onion), *Salvia officinalis* (Sage), *Sambucus nigra* (elderberry), *Capsicum* (cayenne fruit), *Mentha piperita* (peppermint), and/or *Thymus serpyllum* (thyme) and also comprise *Olea europaea* (olive whole leaf), *Lomatium dissectum* (lomatium root), *Rubis idaeus* (red raspberry leaf), and/or *Commiphora myrrha* (myrrh).

In a very particularly preferred embodiment, the remedy according to the present invention comprises sufficient concentrations of ethanol.

In a preferred embodiment, the remedy is provided in a form that is not ingested into the digestive system, but instead facilitates contact between the active agents and the tissues in which the virus is present or through which the virus is likely to enter the body.

In a preferred embodiment, the remedy is administered in the form of nasal spray. This form of provides topical application of the medicaments to the nasal mucosa.

In another preferred embodiment, the remedy is administered in the form of a throat spray. This form of provides topical application of the medicaments to the oral pharyngeal mucosa.

In a particularly preferred embodiment, the remedy administered is in the form of a mouthwash. This form provides topical application of the medicaments to the mouth and throat (specifically, the oral and oral pharyngeal mucosa).

In another particularly preferred embodiment the remedy administered in the form of a lozenge or troche. This form provides topical application of the medicaments to the mouth and/or throat (specifically, the oral and oral pharyngeal mucosa).

In one embodiment, the medicament is applied with a frequency and/or at a dosage which results in the reduction of the duration of the cold.

In another embodiment, the medicament is applied with a frequency and/or at a dosage which results in the reduction of the severity or presence of one or more symptoms of the cold.

In yet another embodiment, the medicament is maintained in contact with the mouth and/or throat for a sufficient length of time that reduction of the duration of the cold is achieved.

In still another embodiment, the medicament is maintained in contact with the mouth and/or throat for a sufficient length of time that reduction of the severity or presence of one or more symptoms of the cold is achieved.

In still another embodiment, the medicament is maintained in contact with the mouth and/or throat for a sufficient length of time that infection by cold viruses is prevented.

In a related embodiment, the maintenance of contact is achieved through the gargling of a mouthwash for a suitable length of time. In fact, reference to a number of the above routes of administration should be considered as including any mode of administering a gargle aliquot of the medicament.

In another related embodiment, the maintenance of contact is achieved by the slow dissolution in the mouth of a suitably sized lozenge and preferably gargling the resultant aqueous composition.

In other embodiments, the remedy may be administered in the form of a sublingual or buccal tablet, a syrup, or sublingual liquid drops or pastilles.

In yet other embodiments, the remedy is administered in a form that is ingested into the digestive tract, such as tablets, capsules, and liquids.

In still another embodiment, the remedy is administered in the form absorbable through the skin.

DETAILED DESCRIPTION OF THE INVENTION

The remedies of the present invention comprise ethanol with or without homeopathic and/or herbal ingredients. The remedies of the present invention preferably do not contain any drugs such as antihistamines, decongestants, pain relievers (e.g., aspirin, acetaminophen, ibuprofen), cough suppressants, expectorants, and analgesics. Consequently, the remedies of the present invention also do not produce the side-effects associated with the use of such drugs. Further, the remedies of the present invention are preferably administered in a form which facilitates contact between the active agents and the tissues in which the virus is present. Thus, the remedies of the present invention are preferably not ingested into the digestive system, which is a further reason that the present remedies have not been associated with any side-effects, and the preferred use of all of the compositions disclosed herein is by gargling. Preferably, the gargling protocol accommodates gargling two-four times per day for at least two days, preferably gargling two-three times per day for at least two days.

Unlike previous remedies, including zinc lozenges, the remedy of the present invention shows a dramatic blockage of cold symptoms within 12-48 hours of illness. The first 12 to 24 hours of a cold is often unavoidable, as this is the time that patients realize that a cold is actually present or on the way.

The remedy of the present invention causes the symptoms to begin to gradually subside as the body's natural immune system is bolstered to block the virus invasion. In many cases, a dramatic or complete blockage of the symptoms is effected within 12 to 24 hours of using the remedy of the present invention.

Remedies according to the present invention may include homeopathic concentrations of one or a combination of *Allium cepa* (red onion), *Salvia officinalis* (Sage), *Sambucus nigra* (elderberry), *Capsicum* (cayenne fruit), *Mentha piperita* (peppermint), *Thymus serpyllum* (thyme), *Aconitum napellus* (monkshood), *Allium sativum* (garlic), *Anas barbariae* (Oscillococcinum), *Euphrasia officinalis* (eyebright), *Ferrum phosphoricum* (ferrous hydrophosphate), *Gelsemium sempervirens* (yellow jassmine), *Kali bichromicum* (potassium dichromate), *Natrum muriaticum* (sodium chloride), *Phytolacca decandra* (poke), *Pulsatilla nigricans* (wind flower), and/or Sulphur (sulphur); and may also include *Olea europaea* (olive whole leaf), *Lomatium dissectum* (lomatium root), *Rubis idaeus* (red raspberry leaf, and/or *Commiphora myrrha* (mrryh), *Trigonella foenum-graecum* (Fenugreek), *Pulmonana officinalis* (lungwort), *Althea officinalis* (marshmellow root tea), *Glycyrrhiza glabra* (licorice), *Ulmus rubra* (slippery elm bark), *Tabebuia avellanedae* (Pau d'arco), *Thymus vulgaris* (thyme), *Melissa officinalis* (lemon oil), *Allium sativum* (garlic), *capsicum annuum* (cayenne fruit). Preferably, remedies according to the present invention include homeopathic concentrations of *Allium cepa* (red onion), *Salvia officinalis* (Sage), *Sambucus nigra* (elderberry), *Capsicum* (cayenne fruit), *Mentha piperita* (peppermint), and/or *Thymus serpyllum* (thyme); and also include *Olea europaea* (olive whole leaf), *Lomatium dissectum* (lomatium root), *Rubis idaeus* (red raspberry leaf), and/or *Commiphora myrrha* (mrryh). Even more preferably, the remedies comprise homeopathic concentrations of at least one of *Allium cepa* (red onion), *Salvia officinalis* (Sage), *Sambucus nigra* (elderberry), *Capsicum* (cayenne fruit), *Mentha pipenta* (peppermint), and/or *Thymus serpyllum* (thyme). Remedies typically also comprise at least one of *Olea europaea* (olive whole leaf), *Lomatium dissectum* (lomatium root), *Rubis idaeus* (red raspberry leaf), and/or *Commiphora myrrha* (mrryh). Most preferably, the remedies of the present invention comprise homeopathic concentration of at least one of *Allium cepa* (red onion), *Salvia officinalis* (Sage), *Sambucus nigra* (elderberry), *Capsicum* (cayenne fruit), *Mentha piperita* (peppermint), and *Thymus serpyllum* (thyme), and at least one of *Olea europaea* (olive whole leaf), *Lomatium dissectum* (lomatium root), *Rubis idaeus* (red raspberry leaf), and/or *Commiphora myrrha* (mrryh).

When *Allium cepa* (red onion), *Salvia officinalis* (Sage), *Sambucus nigra* (elderberry), *Capsicum* (cayenne fruit), *Mentha pipenta* (peppermint), *Thymus serpyllum* (thyme), *Aconitum napellus* (monkshood), *Allium sativum* (garlic), *Anas barbariae* (Oscillococcinum), *Euphrasia officinalis* (eyebright), *Ferrum phosphoricum* (ferrous hydrophosphate), *Gelsemium sempervirens* (yellow jassmine), *Kali bichromicum* (potassium dichromate), *Natrum muriaticum* (sodium chloride), *Phytolacca decandra* (poke), *Pulsatilla nigricans* (wind flower), and/or Sulphur (sulphur) are included in the remedies of this invention, each of these ingredients is preferably prepared to homeopathic concentrations, preferably at a concentration of 1.times. to 60 C, and more preferably at a concentration of from 30.times. to 1.times. Typically, the concentration is 30.times. or 30 C, and most preferably the concentration is 30 C. Preparation of homeopathic ingredients is preferably accomplished through successive dilutions and potentiations, and is well within the ability of one skilled in the art of homeopathy. The prepared homeopathic ingredients are preferably included in the formulation of remedies according to the present invention.

When *Olea europaea* (olive whole leaf), *Lomatium dissectum* (lomatium root), *Rubis idaeus* (red raspberry leaf, and/or *Commiphora myrrha* (mrryh), *Trigonella foenumgraecum* (Fenugreek), *Pulmonana officinalis* (lungwort), *Althea officinalis* (marshmallow root tea), *Glycyrrhiza glabra* (licorice), *Ulmus rubra* (slippery elm bark), *Tabebuia avellanedae* (Pau d'arco), *Thymus vulgaris* (thyme), *Melissa officinalis* (lemon oil), *Allium sativum* (garlic), and/or *capsicum annuum* (cayenne fruit) are included in the remedies of this invention, any of these ingredients may be included at a concentration of from 0.01 to 10% w/v of the remedy. Preferably, any of these ingredients is included at a concentration of 0.1% to 5% w/v of the remedy. Even more preferably, any of these ingredients is included at a concentration of 0.5 to 1% w/v of the remedy. Typically, any of these ingredients is included at a concentration of 1% w/v of the remedy.

Ethanol is included as the base in which homeopathic and/or herbal ingredients may or may not be included and its concentration will range from 20 to 95% w/v. Preferably any food grade or consumer digestible ethanol or spirit ethanol (gin, rum, vodka, etc.) will suffice. Even more preferably, are any of these ingredients at 27 to 40% ethanol (ethanol). Very preferably, the ethanol of choice is vodka with at least a 31 to 37% ethanol content.

These medicaments (ethanol with or without homeopathic and/or herb ingredients extracted and stored in vodka or similar ethanol source), comprise the remedies of the present invention. It is within the ability of one skilled in the art of homeopathy, herbal therapy or supplementation, pharmacology, and/or clinical medicine to optimize the dosage amount, potency, and frequency of administration in order to accomplish objects such as reducing the duration of a cold, reducing the severity of the symptoms of a cold, and/or preventing infection by a cold virus. It is also recognized that these values may differ with such factors as age, weight, and immune status of the subject, severity of illness, and whether the remedy is desired to be used as a treatment for an existing illness or as a prophylaxis.

Other homeopathic and/or herbal medicaments may optionally be included in the remedies of the present invention. It is recognized that non-homeopathic drugs which are commonly used to treat cold symptoms, such as drugs such as antihistamines, decongestants, pain relievers (e.g., aspirin, acetaminophen, ibuprofen), cough suppressants, expectorants, and analgesics, may also be included in the remedies of the present invention. However, preferably, the remedies of the present invention do not contain non-homeopathic drugs.

The remedies of the present invention include the same method but can also comprise nonalcoholic antiviral ingredients.

My invention is similar in claim to Manikas (U.S. Pat. No. 5,286,488) who claimed antiviral plant action from plant oil for herpes and other viruses.

Remedies according to the present invention may include viable concentrations of hydrogen peroxide, baking soda, olive whole leaf, fennel, *eucalyptus*, vinegar, ascorbic acid, food grade acids (citric, malic, oxalic, benoic, quinic, tannic, etc.), the unique combination of ingredients found in fresh ginger, citrus fruits (orange, mandarin, lemon, lime, etc.), cayenne pepper, zinc and honey, or any combination thereof. Each of these ingredients is preferably prepared at standard concentrations normally found in common commerce: hydrogen peroxide, vinegar, food grade acids (citric, malic, oxalic, benoic, quinic, etc.), ascorbic acid, citrus fruits (orange, mandarin, lemon, lime, etc.), and honey. Any of these ingredients may be included at a concentration of from 0.01% to 25% w/v of the remedy. Preferably, any of these ingredients is included at a concentration of from 0.1% to 5% w/v of the remedy. Most preferably, any of these ingredients and particularly the acid ingredients are included at a concentration of from 3% to 5% of w/v of the remedy. The ingredients of this paragraph may even be used to the exclusion of ethanol.

These medicaments (nonalcoholic, antiviral ingredients) comprise the remedies of the present invention. It is within the ability of one skilled in the art of pharmacy or food technology to optimize the dosage amount, potency, and frequency of administration in order to accomplish objects such as reducing the duration of a cold, reducing the severity of the symptoms of a cold, and/or preventing infection by a cold virus. It is also recognized that these values may differ with such factors as age, weight, and immune status of the subject, severity of illness, and whether the remedy is desired to be used as a treatment for an existing illness or as a prophylaxis.

Other nonalcoholic, antiviral medicaments or homeopathic and/or herbal medicaments may optionally be included in the remedies of the present invention. These ingredients include, but are not limited to, *Allium cepa* (red onion), *Salvia officinalis* (sage), *Sambucus nigra* (elderberry), *Capsicum* (cayenne fruit), *Mentha piperita* (peppermint), and/or *Thymus serpyllum* (thyme) and/or *Olea europaea* (olive whole leaf). It is recognized that non-homeopathic drugs which are commonly used to treat cold symptoms, such as drugs such as antihistamines, decongestants, pain relievers (e.g., aspirin, acetaminophen, ibuprofen), cough suppressants, expectorants, and analgesics, may also be included in the remedies of the present invention. However, preferably, the remedies of the present invention do not contain non-homeopathic drugs.

When the remedy is administered as a mouthwash formulation, it is most preferable if the subject does not swallow the mouthwash, but rather gargles with the solution deep in the throat, then spits out the solution. The person should gargle in such a manner that it reaches the sore, irritated, or scratchy portion of the throat. It is best to gargle as soon as a sore, irritated, or scratchy throat is present (preferably within 12-48 hours). The first three dosages of one tablespoon (plus or minus two teaspoons) are taken two hours apart, and the next three dosages are taken four to six hours apart (preferably four hours apart). This method and sequence of dosages is extremely important to the success of the treatment. There is no other cold remedy on the market that recommends such a treatment for the common cold, however, it is this method that allows this invention to work. The mouth may be rinsed, if desired, but the throat is preferably not rinsed. Furthermore, the person should preferably refrain from drinking any liquids for a period of at least one-half hour or more after gargling. It would also be best not to eat which would also interfere with the contact of the medicaments with the throat area.

Preferably, the remedies do not contain any drugs which are not included in the Homeopathic Pharmacopoeia of the United States, or herb or ethanol ingredients that have been used for centuries. Preferably, the remedies do not contain any substances or amounts of substances which require evaluation under an NDA (New Drug Application). The term "drug" is not meant to encompass substances which are herbal or are considered to be foods or dietary supplements by the FDA. Additionally, the term "drug" is not meant to encompass homeopathic concentrations of substances for which an NDA would be required by the FDA in larger concentrations. Homeopathic remedies may exceed 10% ethanol since ethanol is a key ingredient in the manufacturing process.

The remedies of the present invention preferably do not include interferon, interferon inducers, propanediamine, enviroxime, dichloroflaven, 2 {(1,5101-tetrahydro-3H-thiazolo[3,4b]isoquinolin-3-ylidene)amino}-4-thiaz oleacetic acid (S) or sodium polyacrylate. Most preferably, the remedies do not contain these substances at any concentration, i.e., most preferably, these substances are absent from the remedies.

A "common cold" or simply "cold" is that condition generally associated with the term, including any or all symptoms thereof; such as nasal drainage, nasal congestion, headache, fever, myalgia, sneezing, sore throat, scratchy throat, cough and hoarseness, and, occasionally, bronchial-sinusitis symptoms. A sore throat is commonly the first sign that a subject has been infected by a cold virus and is a sign that the virus has lodged itself in the tender throat lining. The virus grows through the surface to the sensitive nerve endings resulting in inflammation and soreness. Mucus flow increases trying to sluff the throat irritant away, but the mucus and the debris from the dead cells drop down into the lungs, spreading the virus and resulting in further symptoms, such as a hacking cough. Post nasal drip follows. Swelling in the back of the throat can also block Eustachian tubes making it difficult to hear. Unfortunately, some individuals suffer more seriously from colds. Sinuses may become blocked by the excessive swelling of membranes resulting in a severe sinus headache. If recovery is delayed and the virus spreads to the lungs bronchitis may develop, and may, especially in immune-compromised individuals, turn into pneumonia . . . a potential cause of death.

For the purposes of this disclosure, a subject who is described as "suffering from a cold" is equivalent to a subject who is described as "suffering from the symptoms of a cold," and both phrases refer to a subject who is experiencing some or all of the above-listed symptoms of the common cold.

The preparations of the invention are suitable for the treatment of an infection by a virus generally recognized as causing, or being associated with, the common cold or the symptoms thereof. The common cold is most commonly caused by rhinoviruses, and the second leading cause of the common cold are the coronaviruses. Other types of virus recognized as causing or being associated with the common cold include adenoviruses, influenza viruses, parainfluenza viruses, respiratory syncytial viruses, enteroviruses, echoviruses, and coxsackieviruses.

While it is believed that the preparations of the invention are actually virostatic or viricidal, it will be appreciated that this is not known for certain, and it is possible that only symptomatic relief is obtained. Specifically, without wanting to be limited to a specific theory or mechanism of action of the remedies of the present invention, the inventor believes that the remedies function by killing the virus, directly or indrectly with antiviral ingredients (especially the ethanol) as well as by promoting and enabling the body's own immune system to better destroy, inactivate, and/or prevent the spread of the virus. Likewise, and again without wishing to be so limited by a specific theory, the inventor believes that the remedies prevent infection by destroying and/or inactivating virus with antiviral ingredients before the virus can begin to damage and replicate in tissues and/or by activating promoting and enabling the body's own immune system to better destroy, inactivate, and/or prevent the spread of the virus.

Particularly, the preparations of the invention are suitable for use any time from when the subject first notices any signs of a cold until the symptoms have cleared up. In fact, in some cases, such as for persistent sufferers, or where individually desired, it may be appropriate to continue treatment indefinitely, in the absence of contraindications. Thus, the remedies of the present invention are suitable for acute treatment, chronic treatment, and prophylaxis. Both acute and chronic treatment and prophylaxis will be encompassed by the term "treatment" for purposes of the present disclosure, unless indicated otherwise, either explicitly or from context. The terms "treatment" and "prophylaxis" are used in a broad sense, and extend from symptomatic relief to cure of the infection to general preventative therapy, especially in winter, or for particularly prone individuals.

A "subject in need of treatment" includes subjects who have contracted a virus which may cause a common cold, subjects who exhibit symptoms of the common cold, subjects who are suffering from a cold or from the symptoms of a cold, and those subjects who particularly wish to take preventative measures to avoid infection by a cold virus. Subjects who particularly wish to take preventative measures to avoid infection by a cold virus include those subjects who are or believe they are prone to infection by cold virus and those subjects who are especially vulnerable to suffering severe effects from a cold virus. The especial vulnerability of the latter population of subjects may be due to conditions including old age, young age, or immunocompromization. In the case of subjects who particularly wish to take preventative measures to avoid infection by a cold virus, the remedies of the present invention may be given as a prophylactic.

In order to test the efficacy of the cold repellant of the present invention, the inventor conducted 18 informal case studies and their results are provided in the Examples below. As can be seen from the Examples, in general, best results seem to be obtained when treatment is commenced immediately when there is any suspicion of a cold. Specifically, the cold and its accompanying cascade of cold symptoms is most effectively repelled by the remedy of the present invention when it is administered within the first 12 to 24 hours of the first cold symptom—most commonly, this first symptom is a sore throat.

When the remedies of the present invention are administered acutely, they are most preferably used beginning at the earliest signs of an oncoming cold. For example, a sore throat commonly indicates the onset of a cold. The remedy preferably is used three times per day (e.g., every 4-6 hours, preferably morning, midday, and evening). Preferably, the use of the remedy is continued for two days. However, the remedies may be used for longer periods, e.g., until the cold symptoms are completely gone. It is noted that in may cases, cold symptoms are alleviated or eliminated within two days after commencement of use of the remedy, and so two days is the recommended limit of administration because continued presence of symptoms may indicate a condition other than the common cold.

When the remedies of the present invention are administered prophylactically or chronically, they may be used at lower doses or with lower frequency than is desirable for acute administration.

The remedies of the present invention are preferably provided in a form that is not ingested into the digestive system, but instead facilitates contact between the active agents and the tissues in which the virus is present or through which the virus is likely to enter the body. A preferred form is a nasal spray. This form provides topical application of the medicaments to the nasal mucosa. Another form is in the topical application of the medicament in the form of a throat spray that applies to the oral pharyngeal area. A particularly preferred form is a mouthwash. Another particularly preferred form is a lozenge. These particularly preferred forms (mouthwash and lozenge) each provide topical application of the medicaments to the mouth and/or throat (specifically, the oral and oral pharyngeal mucosa).

The term "gargling" is to be interpreted broadly and encompasses gargling, swishing, simply holding liquid in the mouth and the back of the throat, and the like.

The remedy may also be administered in the form of a sublingual or buccal tablet, a syrup, or sublingual liquid drops or pastilles. These forms also provide for topical application of the medicaments to the mouth and/or throat.

The medicament is preferably maintained in contact with the mouth and/or throat for a sufficient length of time that reduction of the duration of the cold is achieved, reduction of the severity or presence of one or more symptoms of the cold is achieved, and/or prevention of infection by cold viruses is achieved. Maintenance of contact may preferably be achieved through the gargling of a mouthwash for a suitable length of time. Maintenance of contact may also preferably be achieved by the slow dissolution in the mouth of a suitably sized lozenge. Maintenance of contact may also be achieved by dissolving a suitable size or amount of, e.g., pastilles, drops, or sub-lingual or buccal tablets in the mouth.

The suitable length of contact, and thus the time of gargling, size of lozenge or tablet, or number of pastilles, is readily ascertainable to one of skill in the arts of homeopathy, herbal, and/or clinical medicine. Further, as with the concentrations of active ingredients to be employed (see above), the length of contact may differ with the characteristics of the subject and the object(s) to be achieved.

The remedy may also be administered in a form that is ingested into the digestive tract, such as tablets, capsules, and liquids; and may also be administered in the form of an injection or in a form absorbable through the skin.

Methods for formulating nasal sprays, throat sprays, mouthwashes, lozenges, sublingual tablets, buccal tablets, syrups, pastilles, drops, tablets, capsule, and liquids that are suitable carriers for medicaments are well known to the art of pharmaceutical formulation. One skilled in this art is also well aware of methods for preparing injectable forms of medicaments, as well as methods for preparing forms, such as skin-patches and creams, which allow for the absorption of medicaments through the skin.

The formulations may contain a predetermined amount or concentration of at least one medicament according to the present invention. These formulations can be prepared by any suitable pharmaceutical method. The formulations also may vary can vary with the condition and age of the patient and with the object(s) sought to be achieved. The amounts and/or concentrations of medicament to be included may be determined as indicated herein.

When formulating a mouthwash, lozenge, pastilles, or other form which is to be held in the mouth, it may be desirable to include at least one sweetener in the formulation. Examples of suitable sweeteners may be sugars such as fructose, lactose, and sucrose and sugar substitutes such as saccharin. Formulations to be held in the mouth may also desirably contain flavoring agents such as, for example, anise, anethole, eucalyptol, wintergreen, licorice, clove, cinnamon, spearmint, cherry, lemon, orange, lime, menthol, peppermint and various combinations thereof.

In formulations suitable for nasal administration, the ethanol, herbal, homeopathic, and, optionally, other active ingredients are formulated with a liquid carrier, such as those used in a conventional nasal spray or nasal drops.

In formulations suitable for throat administration, the ethanol, herbal, homeopathic, and, optionally, other active ingredients are formulated with a liquid carrier, such as those used in a conventional throat spray.

In a particularly preferred embodiment, the remedy is administered in the form of a mouthwash. Methods for making mouthwashes are well-known in the art. Non-limiting examples of mouthwash compositions, to which the ethanol (at sufficient concentrations) with or without herbal, homeopathic, and, optionally, other active ingredients may be added, are as follows.

- 0 to 2% by weight of sodium saccharin, or an amount sufficient to provide a sweetening effect equivalent thereto of a sweetening agent; and
- 0.01 to 1% by weight flavoring agent (such as peppermint oil, spearmint oil, and/or mixtures thereof)
- 20-95% alcohol (ethanol)
- q.s. water
- 5 to 15% v/v sorbitol
- 0.5 to 2.5% w/v surfactant
- 0.25 to 1% w/v sodium chloride
- 0.05 to 0.2% w/v insoluble saccharin
- 0.01 to 0.25% w/v flavoring (such as menthol, thymol, eucalyptol, peppermint oil, and/or mixtures thereof)
- 0.1 to 2% w/v sodium ricinoleate
- 20 to 95% v/v alcohol (ethanol)
- q.s. water When the remedy is administered as a mouthwash formulation, it is most preferable if the subject does not swallow the mouthwash, but rather gargles with the solution deep in the throat, then spits out the solution. The mouth may be rinsed, if desired, but the throat is preferably not rinsed. Further, the subject preferably refrains from drinking any liquids for a period of at least one half hour or more after gargling.

In another particularly preferred embodiment the remedy administered in the form of a lozenge. Formulation of lozenges is well known in the art of pharmaceuticals. As an example, the herbal, homeopathic, and, optionally, other active ingredients may be mixed with a flavored base, usually sucrose and *acacia* or tragacanth and formulated into lozenges by standard methods.

In other embodiments, the remedy may be administered in the form of a sublingual or buccal tablet, a syrup, or sublingual liquid drops or pastilles. Methods of preparing such formulations are well-known in the art of pharmaceuticals.

In yet other embodiments, the remedy is administered in a form that is ingested into the digestive tract, such as tablets, capsules, and liquids. For example, the remedy may be administered in the form of gel capsules. It will be recognized that any known means of producing gel capsules can be used in accordance with the present invention. As another example, the remedy may be administered in the form of pressed tablets. Compressed tablets can be prepared by, for example, mixing the herbal, homeopathic, and, optionally, other active ingredients with dry inert ingredients such as carboxymethyl cellulose and compressing or molding in a suitable machine. The tablets optionally can be coated or scored and can be formulated so as to provide slow or controlled release of the active ingredients therein.

In still another embodiment, the remedy is administered in the form absorbable through the skin.

All publications and patent applications mentioned in this specification are herein incorporated by reference to the same extent as if each individual publication or patent application had been specifically and individually indicated to be incorporated by reference.

It is possible to use various commercial product intended for oral ingestion as a gargle according to the present invention. At this writing, one such commercial product is sold under the name, AIRBORNE, and contains per serving 5,000 I.U. Vitamin A, 1,000 mg Vitamin C, 30 I.U. Vitamin E, 40 mg Magnesium Sulfate, 8 mg Zinc Sulfate, 15 mcg Sodium Selenite, 3 mg Manganese Gluconate, 75 mg Potassium Bicarbonate, 350 mg herbal extracts (*Lonicera*, Forsythia, Schizonepeta, Ginger, Chinese Vitex, Isatis Root, and *Echinacea*), along with citric acid, sorbitol, sodium bicarbonate, natural orange flavor, polyethylene glycol, aspartame, mineral and canola oil and riboflavin. Because of the high strength of the constituents in AIRBORNE, which is intended as an oral dietary supplement, typical gargle aliquot amounts of AIRBORNE may be used for gargling (instead of an oral ingestible composition) to reduce the symptoms of the common cold.

Overall, it is important to realize that many of the compositions described herein may already be known as oral compositions for ingestion, but that the benefits of using them as a gargle solution or product have been first recognized and promoted here.

The following examples are illustrative.

EXAMPLES

In order to facilitate a more complete understanding of the invention, a number of Examples are provided below. However, the scope of the invention is not limited to specific embodiments disclosed in these Examples, which are for purposes of illustration only.

In each of the following examples, the subjects were administered one tablespoon (15 mL) of remedy comprising ethanol with or without homeopathic and/or herb ingredients adequately preserved in ethanol) consisting of one or a combination of *Allium cepa* (red onion), *Salvia officinalis* (Sage), *Sambucus nigra* (elderberry), *Capsicum* (cayenne fruit), *Mentha piperita* (peppermint), and/or *Thymus serpyllum* (thyme); and also comprising *Olea europaea* (olive whole leaf), *Lomatium dissectum* (lomatium root), *Rubis idaeus* (red raspberry leaf), and/or *Commiphora myrrha* (mrryh) in a mouthwash formulation three times a day for at least two days.

Example 1

The inventor, a female aged 38 at the time of this trial, administered the remedy to herself. She was suffering the symptoms of a common cold that was of 12 hours old duration at the time of the administration. The inventor's cold was blocked within 24 hours of treatment, meaning that the symptoms abated and did not recur.

Example 2

The trial of Example 1 was again conducted when the inventor later suffered from an unrelated cold, and the cold was again blocked within 24 hours of treatment.

Example 3

The remedy was administered to a 26 year old male suffering from the symptoms of a common cold. The cold was blocked within 24 hours of treatment.

Example 4

The remedy was administered to a 21 year old male suffering from the symptoms of a common cold. The cold was blocked within 24 hours of treatment.

Example 5

The trial of Example 1 was again conducted when the inventor later suffered from an unrelated cold, and the cold was again blocked within 24 hours of treatment.

Example 6

The remedy was administered to a 35 year old female who had been suffering from a cold for a week before treatment. The woman's symptoms were so much reduced within 24 hours of treatment that she even visibly appeared to be recovering. In this case, 4 days passed before the symptoms were completely gone. The most likely reason that more time than in previous trials was required to completely clear the symptoms is that the cold had had 7 days to spread through the subject's body and affect many cells and tissues before treatment was begun.

Example 7

The remedy was administered to a 50 year old female who had been suffering from an especially severe cold for a week before treatment. The woman's symptoms were so much reduced within 24 hours of treatment that she even visibly appeared to be recovering. In this case, 4 days passed before the symptoms were completely gone. The most likely reason that more time than in previous trials was required to completely clear the symptoms is that the cold had had 7 days to spread through the subject's body and affect many cells and tissues before treatment was begun.

Example 8

The remedy was administered to a 40 year old male who had just begun suffering from the symptoms of a common cold. Although the symptoms had just begun to appear in the subject, the subject's son had been suffering from an especially severe cold for some time. Two strong doses were administered to this subject within 10 minutes, and the cold was blocked within 12 hours of treatment.

Example 9

The remedy was administered to an 11 year old male who had been suffering from the symptoms of a common cold for more than two days. The usual duration of the common cold in this subject is known to be 10 days. The cold during which this subject received the remedy of the present invention was reduced to 4 days total duration.

Example 10

The remedy was administered to a 48 year old male who had just begun suffering from the symptoms of a common cold. Although the symptoms had just begun to appear in the subject, the subject had just returned from a holiday during which he shared living quarters with several friends suffering from colds. The cold was blocked after one day following administration.

Example 11

The remedy was administered to a 37 year old female suffering from the symptoms of a common cold. This subject is known to be prone to numerous illnesses, and who often experiences relapses or reoccurrences of colds, often developing several colds in a row. The cold was blocked and she did not experience another reoccurrence until 4 weeks later.

Example 12

The remedy was administered to a 40 year old male suffering from the symptoms of a common cold. In this trial, the cold was not blocked. However, this subject is known to suffer from allergies and chronic sinusitis. Therefore, it is likely that an allergic reaction of bacterial infection was the cause of the symptoms.

Example 13

The remedy was administered to a 10 year old female suffering from the symptoms of a common cold. The cold was blocked.

Example 14

The remedy was administered to the subject of Example 11 when she later suffered from an unrelated cold. The cold was blocked with no reoccurance for at least 3 months.

Example 15

The remedy was administered to a 46 year old female who had just begun suffering from the symptoms of a common cold. The cold was blocked within 48 hours.

Example 16

The remedy was administered to the subject of Example 10 when he later began to suffer the symptoms of an unrelated cold, possibly spread by Example 15. The cold was blocked within 48 hours.

Example 17

The remedy was administered to a 50 year old male who had been severely suffering from the symptoms of a common cold for 12 hours. The cold was blocked within 24 hours.

Example 18

The remedy was administered to the subject of Example 17 when he later began to suffer the symptoms of an unrelated cold. Again the cold was blocked within 24 hours.

Example 19

InVitro Studies

Results of antiviral invitro testing performed at baylor college of medicine department of molecular virology & microbiology.

TABLE 1

Results of antiviral activity testing various materials
against rhinovirus (Rhinovirus 14 in KB cells).

| Material | Toxicity | Virus Inhibition | Selective Inhibition |
|---|---|---|---|
| Olive Whole Leaf | 3 | 7 | 16 |
| Garlic | 4 | 4 | 0 |
| Cayenne | 4 | 4 | 0 |
| Ginger | 4 | 4 | 0 |
| Ascorbic Acid | 4 | 4 | 0 |
| Baking Soda | 2 | 4 | 2 |
| Citric Acid | 6 | 6 | 0 |
| Malic Acid | 6 | 6 | 0 |
| Hydrogen Peroxide | 7 | 7 | 0 |

Tissue control: all negative
Virus control: all 4+ positive (4 values and above indicate excellent antiviral activity)

TABLE 2

Results of antiviral activity testing various materials
against influenza virus (Influenza A/Hong Kong/68 (H3N2)
in Madin Darby Canine Kidney (MDCK) cells).

| Material | Toxicity | Virus Inhibition | Selective Inhibition |
|---|---|---|---|
| Traditional Chinese Medicine Tea | 2 | 10 | 8 |
| Baking Soda | 0 | 2 | 4 |
| Food Grade Acid | 2 | 4 | 4 |
| Garlic | 4 | 5 | 1 |
| Cayenne | 4 | 5 | 1 |
| Ginger | 4 | 4 | 0 |
| Citric Acid | 6 | 6 | 0 |
| Malic Acid | 6 | 6 | 0 |
| Hydrogen Peroxide | 6 | 6 | 0 |

Tissue control: all negative
Virus control: all 4+ positive (4 values and above indicate excellent antiviral activity)

TABLE 3

Results of antiviral activity testing various
materials against Influenza (Parainfluenza
Virus (PIV) Type 3 in Hep2 cells).

| Material | Toxicity | Virus Inhibition | Selective Inhibition |
|---|---|---|---|
| Olive Whole Leaf | 2 | 4 | 4 |

Tissue control: all negative
Virus control: all 4+ positive (4 values and above indicate excellent antiviral activity)

EXAMPLES

In order to facilitate a more complete understanding of the invention, a number of Examples are provided below. However, the scope of the invention is not limited to specific embodiments disclosed in these Examples, which are for purposes of illustration only. In each of the following Examples, the subjects were administered one tablespoon (15 ml) of remedy in a mouthwash formulation three times a day for at least two days comprising:

Citric Acid

Example 1

The remedy was administered to a male (RB) and he recovered from his cold within three days.

Example 2

The remedy was administered to a female (KM) within 34 hours of her cold and she recovered within one day.

Example 3

The remedy was administered to a female (CS) within 24 hours of her cold and she recovered within four days.

Example 4

The remedy was administered to a female (JM) within 13 hours of her cold and she recovered from her cold within two days.

Example 5

The remedy was administered to a male (GF) within 15 hours of his cold and he recovered within ten days, but he stated that his colds usually last two to three weeks.

Example 6

The remedy was administered to a female (CP) within 30 hours of her cold and she recovered within five days.

Example 7

The remedy was administered to a male (SP) within 14 hours of his cold and he recovered from his cold within four days.

Example 8

The remedy was administered to a female (KM) within 34 hours of her cold and she recovered within one day.

Ascorbic Acid

Example 1

The remedy was administered to a female and she recovered from her cold within one day.

Example 2

The remedy was administered to a male within 12 hours of his cold and he recovered within one day.

Example 3

The remedy was administered to a female within 24 hours of her cold and she recovered within two days.

Baking Soda

Example 1

The remedy was administered to a female (KH) within 22 hours of her cold and she recovered from her cold within one day.

Example 2

The remedy was administered to a male (JO) within 16 hours of his cold and he recovered within two days.

Example 3

The remedy was administered to a male (SM) within 48 hours of his cold and he recovered within two days.

Example 4

The remedy was administered to a male (KA) within 13 hours of his cold and he recovered from his cold within three days.

Example 5

The remedy was administered to a male (MR) within 96 hours of his cold and he recovered within three days.

Example 6

The remedy was administered to a male (JF) within 11 hours of his cold and he recovered within two days.

DESCRIPTION OF THE PREFERRED EMBODIMENT(S)

This invention provides methods and compounds for reducing the presence, duration, and severity of a common cold and of its symptoms by the administration of ethanol with or without homeopathic and/or herbal medicaments.

This invention provides methods and compounds for reducing the presence, duration, and severity of a common cold and of its symptoms by the administration of nonalcoholic, antiviral remedy comprising of ingredients that are antiviral when applied topically—hydrogen peroxide, baking soda, vinegar, garlic, olive whole leaf, fennel, *eucalyptus*, zinc, ascorbic acid, food grade acids (citric, malic, oxalic, benoic, quinic, tannic, etc.), the unique combination of ingredients found in fresh ginger, citrus fruits (orange, mandarin, lemon, lime, etc.), and honey, or any combination thereof.

It is an object of this invention to provide effective treatments for the treatment of the common cold and its symptoms. Specifically, it is an object of this invention to provide remedies which reduce the duration of the cold, which reduce the severity or duration of one or more symptoms of the cold, and/or which prevent the common cold.

It is another object of this invention to overcome the problems and disadvantages associated with currently known approaches to treating the common cold and its symptoms.

Prior treatments for the cold have focused on alleviation of its symptoms. Very few remedies have had any success in reducing the duration of the cold. Further, prior treatments almost always contain drugs which cause side effects, which can be as debilitating as the cold itself. Unexpectedly, the present inventor has discovered that certain medicaments (ethanol with or without homeopathic and/or herb ingredients) can reduce the duration of the cold itself, as well as reducing the severity of the symptoms of the cold, and may also prevent infection by cold viruses. The remedy's active ingredient is ethanol with or without homeopathic and/or herb ingredients that are without known side effects and/or are given at homeopathic dosages, which appear to produce no side effects. The remedies of this invention therefore represent a novel treatment for the common cold, which treatment overcomes many of the disadvantages of the prior remedies.

In one embodiment, remedies according to the present invention include homeopathic concentrations of *Allium cepa* (red onion), *Salvia officinalis* (Sage), *Sambucus nigra* (elderberry), *Capsicum* (cayenne fruit), *Mentha piperta* (peppermint), and/or *Thymus serpyllum* (thyme); and also include perhaps one or a combination of the following ingredients: *Olea europaea* (olive whole leaf) *Lomatium dissectum* (lomatium root), *Rubis idaeus* (red raspberry leaf), and/or *Commiphora myrrha* (mrryh), *Trigonella foenum-graecum* (Fenugreek), *Pulmonaeia officinalis* (lungwort), *Althea officinalis* (marshmallow root tea), *Glycyrrhiza glabra* (licorice), *Ulmus rubra* (slippery elm bark), *Tabebuia avellanedae* (Pau d'arco), *Thymus vulgaeis* (thyme), *Melissa officinalis* (lemon oil), *Allium sativum* (garlic), and/or *capsicum annuum* (cayenne fruit).

In a preferred embodiment, remedies according to the present invention include homeopathic concentrations of *Allium cepa* (red onion), *Salvia officinalis* (Sage), *Sambucus nigra* (elderberry), *Capsicum* (cayenne fruit), *Mentha piperita* (peppermint), and/or *Thymus serpyllum* (thyme); and may also include one or a combination of *Olea europaea* (olive whole leaf), *Lomatium dissectum* (lomatium root), *Rubis idaeus* (red raspberry leaf), and/or *Commiphora myrrha* (mrryh).

In another preferred embodiment, the remedies comprise homeopathic concentrations singly and/or in combination of *Allium cepa* (red onion), *Salvia officinalis* (Sage), *Sambucus nigra* (elderberry), *Capsicum* (cayenne fruit), *Mentha piperita* (peppermint), *Thymus serpyllum* (thyme), and/or olive whole leaf (*Olea eruopaea*).

In yet another preferred embodiment, the remedies according to the present invention comprise one or a combination of *Olea europaea* (olive whole leaf), *Lomatium dissectum* (lomatium root), *Rubis idaeus* (red raspberry leaf), and/or *Commiphora myrrha* (mrryh).

In a particularly preferred embodiment, the remedies according to the present invention comprise homeopathic concentrations of at least one of *Allium cepa* (red onion), *Salvia officinalis* (Sage), *Sambucus nigra* (elderberry), *Capsicum* (cayenne fruit), *Mentha pipefita* (peppermint), and/or *Thymus serpyllum* (thyme) and also comprise at least one of *Olea europaea* (olive whole leaf), *Lomatium dissectum* (lomatium root), *Rubis idaeus* (red raspberry leaf), and/or *Commiphora myrrha* (mrryh).

In another particularly preferred embodiment, the remedies according to the present invention comprise homeopathic concentrations of *Allium cepa* (red onion), *Salvia officinalis* (Sage), *Sambucus nigra* (elderberry), *Capsicum* (cayenne fruit), *Mentha piperita* (peppermint), and/or *Thymus serpyllum* (thyme) and also comprise *Olea europaea* (olive whole leaf), *Lomatium dissectum* (lomatium root), *Rubis idaeus* (red raspberry leaf), and/or *Commiphora myrrha* (mrryh).

In a very particularly preferred embodiment, the remedy according to the present invention comprises sufficient concentrations of ethanol.

In a preferred embodiment, the remedy is provided in a form that is not ingested into the digestive system, but instead facilitates contact between the active agents and the tissues in which the virus is present or through which the virus is likely to enter the body.

In a preferred embodiment, the remedy is administered in the form of nasal spray. This form of provides topical application of the medicaments to the nasal mucosa.

In another preferred embodiment, the remedy is administered in the form of a throat spray. This form of provides topical application of the medicaments to the oral pharyngeal mucosa.

In a particularly preferred embodiment, the remedy administered is in the form of a mouthwash. This form provides topical application of the medicaments to the mouth and throat (specifically, the oral and oral pharyngeal mucosa).

In another particularly preferred embodiment the remedy administered in the form of a lozenge or troche. This form provides topical application of the medicaments to the mouth and/or throat (specifically, the oral and oral pharyngeal mucosa).

In one embodiment, the medicament is applied with a frequency and/or at a dosage which results in the reduction of the duration of the cold.

In another embodiment, the medicament is applied with a frequency and/or at a dosage which results in the reduction of the severity or presence of one or more symptoms of the cold.

In yet another embodiment, the medicament is maintained in contact with the mouth and/or throat for a sufficient length of time that reduction of the duration of the cold is achieved.

In still another embodiment, the medicament is maintained in contact with the mouth and/or throat for a sufficient length of time that reduction of the severity or presence of one or more symptoms of the cold is achieved.

In still another embodiment, the medicament is maintained in contact with the mouth and/or throat for a sufficient length of time that infection by cold viruses is prevented.

In a related embodiment, the maintenance of contact is achieved through the gargling of a mouthwash for a suitable length of time.

In another related embodiment, the maintenance of contact is achieved by the slow dissolution in the mouth of a suitably sized lozenge.

In other embodiments, the remedy may be administered in the form of a sublingual or buccal tablet, a syrup, or sublingual liquid drops or pastilles.

In yet other embodiments, the remedy is administered in a form that is ingested into the digestive tract, such as tablets, capsules, and liquids.

In still another embodiment, the remedy is administered in the form absorbable through the skin.

In still another embodiment, the remedy is administered in the form of a nasal spray.

It is possible to understand the above disclosure best in light of the following. It is believed that the primary commercial embodiment of the subject matter of this continuation-in-part specification is the composition intended for gargling, which contains nonalcoholic ingredient(s) of one or more kinds. In general, the original alcohol-containing formula is intended for adults and the nonalcoholic version of the gargle is best suited for use by children. The intention is to treat upper respiratory infections by eradicating the virus (rhinovirus, influenza, and other upper respiratory tract viruses) via a topical approach using a gargle that is repeatedly applied to the oral and naso-pharyngeal mucous membrane areas, preferably at least two times per day for at least two days, more preferably three times a day for at least two days. Such a treatment "blocks" the virus by preventing the virus from replicating and causing advanced upper respiratory tract symptoms.

Not that any and all substances would have the above-described anti-upper-respiratory tract action, but certain ones that target the susceptibilities of rhinovirus, influenza viruses and other upper-respiratory viruses are those that are meant in this patent application. In its most preferred form, the focus of the invention is not upon the discovery of whether certain agents are antiviral, antimicrobial, etc., or not, but on actual using the ingredients as a gargle as an effective way of reducing the symptoms and duration of the common cold.

In this light, a particularly preferred herbal contains one more more plant parts which themselves contain ingredients which are antiviral, astringent, acidic or antibiotic in nature. Examples include but are not limited to citrus fruits (orange, mandarin, lemon, lime, etc.), plant acids (citric acid, etc.), food grade acids (malic, oxalic, benzoic, quinic, tannic, and others), teas, vinegar, olive leaf, garlic, cayenne, fennel, *eucalyptus*, etc. Mineral salts are also contemplated if they are antiviral, astringent, acidic or antibiotic in nature, particularly but without limitation zinc and zinc salts.

When the above substances, or similar ones in nature, are applied to the oral and oral pharyngeal mucous membranes, then their antiviral effect "blocks" the upper respiratory tract virus from progressing into a full infection. Duration of the upper respiratory tract infection is reduced.

When food-grade acids form the primary active ingredient in the gargle composition, the range of concentrations may be 0.05-20.0% food grade acid, balance water, or preferably 0.05-10.0% food grade acid, more preferably 3-4%. By "food grade" acids are meant all the edible acids described throughout this specification. These same acids in the same amounts may be mixed with ethanol as well. When olive leaf is used for its active ingredient oleuropein as the primary active ingredient in the gargle composition, the oleuropein should be present in the amount of 3-20% oleuropein, preferably 6-15% oleuropein, most preferably about 6% oleuropein.

The invention claimed is:

1. An oral treatment method to reduce the duration of common cold symptoms, comprising: administering to a patient suffering from the common cold an oral composition in a form suitable for gargling, said oral composition consisting essentially of an aqueous composition containing an extract of olive leaf wherein said oral composition contains 3-20% oleuropein, in an amount sufficient for the patient to gargle said composition, and further wherein said patient gargles the composition; and repeating the administration of said oral composition at least three times per day or at least every 4-6 hours for at least two days.

2. The oral treatment method according to claim 1 wherein said oral composition is a mouthwash.

3. The oral treatment method according to claim 1 wherein said oral composition contains 6-15% oleuropein.

4. The oral treatment method according to claim 1 wherein said oral composition contains about 6% oleuropein.

5. The oral treatment method according to claim 1 wherein said amount sufficient for said patient to gargle said composition is approximately 15 mL.

6. An oral treatment method to reduce the duration of common cold symptoms, comprising: administering to a patient suffering from the common cold, with administration beginning within the first 12 to 24 hours of the first cold symptom, an oral composition in a form suitable for gargling, said oral composition consisting essentially of an aqueous composition containing an extract of olive leaf wherein said oral composition contains 3-20% oleuropein, in an amount sufficient for the patient to gargle said composition, and further wherein said patient gargles the composition; and repeating the administration of said oral composition at least three times per day or at least every 4-6 hours for at least two days.

* * * * *